United States Patent

Friebe et al.

[11] Patent Number: 5,696,155
[45] Date of Patent: Dec. 9, 1997

[54] DIBENZ[B,E]OXEPIN DERIVATIVES AND PHARMACEUTICAL AGENTS WHICH CONTAIN THEM

[75] Inventors: Walter-Gunar Friebe; Werner Scheuer, both of Mannheim; Ulrich Tibes, Frankfurt, all of Germany

[73] Assignee: Boehringer Mannheim BmbH, Mannheim, Germany

[21] Appl. No.: 632,473

[22] PCT Filed: Oct. 22, 1994

[86] PCT No.: PCT/EP94/03479

§ 371 Date: Sep. 10, 1996

§ 102(e) Date: Sep. 10, 1996

[87] PCT Pub. No.: WO95/11906

PCT Pub. Date: May 4, 1995

[30] Foreign Application Priority Data

Oct. 26, 1993 [DE] Germany ............ 43 36 491.8

[51] Int. Cl.⁶ ............... A61K 31/335; C07D 313/12
[52] U.S. Cl. .............................. 514/450; 549/348
[58] Field of Search ..................... 549/348; 514/450

[56] References Cited

FOREIGN PATENT DOCUMENTS 436025  7/1991  European Pat. Off. .

*Primary Examiner*—Bernard Dentz
*Attorney, Agent, or Firm*—Nikaido, Marmelstein, Murray & Oram LLP

[57] ABSTRACT

Compounds of formula I

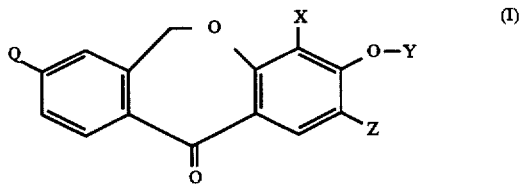

in which

Q denotes hydrogen, a hydroxy group or a $C_1$ to $C_8$ alkoxy group which can be substituted if desired, by carboxyl or $C_1$ to $C_6$ alkoxycarbonyl and either Y and Z together form a group

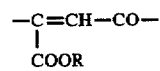

and X represents hydrogen, $C_1$ to $C_6$ alkyl or $C_2$ to $C_6$ alkenyl or Y and X together form a group

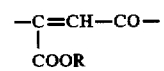

or an alkylene residue of 2–4 carbon atoms and Z represents hydrogen, $C_1$ to $C_6$ alkyl or $C_1$ to $C_6$ alkanoyl, where R denotes hydrogen or a $C_1$ to $C_6$ alkyl residue as well as physiologically tolerated salts thereof, processes for their production and pharmaceutical agents containing these compounds for the treatment of inflammatory diseases and allergic diseases.

7 Claims, No Drawings

DIBENZ[B,E]OXEPIN DERIVATIVES AND PHARMACEUTICAL AGENTS WHICH CONTAIN THEM

This application is a 371 of PCT/EP94/03479 filed Oct. 22, 1994.

The present invention concerns new dibenz[b,e]oxepin derivatives, processes for their production and pharmaceutical agents which contain these compounds.

The invention concerns dibenz[b,e]oxepin derivatives of the general formula I

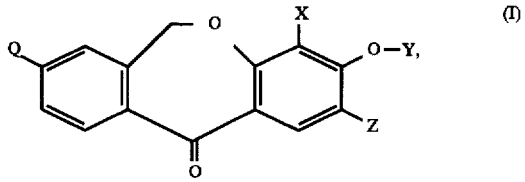

in which

Q denotes hydrogen, a hydroxy group or a $C_1$ to $C_8$ alkoxy group which can be substituted if desired, by carboxyl or $C_1$ to $C_6$ alkoxycarbonyl and either Y and Z together form a group

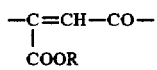

and

X represents hydrogen, $C_1$ to $C_6$ alkyl or $C_2$ to $C_6$ alkenyl or

Y and X together form a group

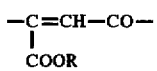

or an alkylene residue of 2–4 carbon atoms and

Z represents hydrogen, $C_1$ to $C_6$ alkyl or $C_1$ to $C_6$ alkanoyl, where

R denotes hydrogen or a $C_1$ to $C_6$ alkyl residue as well as physiologically tolerated salts thereof.

The compounds of formula I have valuable pharmacological properties, in particular they can inhibit the activity of phospholipases. They are therefore suitable for the treatment of acute and chronic, allergic, non-allergic and traumatic and inflammatory diseases such as rheumatoid arthritis, osteoarthritis, ulcerative colitis, acute pancreatitis, contact dermatitis, inflammatory and allergic respiratory tract diseases, septic shock, allergic shock, serum sickness, autoimmune diseases, graft-versus-host reactions, host-versus-graft diseases, ischaemic or thrombotic diseases such as coronary infarction or cerebral infarction.

Alkyl residues in the said groups alkyl, alkoxy and alkanoyl can be straight-chained or branched. Preferred residues are the methyl, ethyl, propyl, isopropyl, n-butyl, isobutyl, tert.butyl, n-pentyl and 3-pentyl residues.

Alkylene residues can be straight-chained or branched. Preferred residues are 1,2-ethylene, 1,3-propylene, 1,2-propylene and 1,4-butylene.

Apart from the compounds mentioned in the examples, the invention also relates in particular to all substances which have any possible combination of the substituents mentioned in the examples.

The process according to the invention for the production of compounds of formula I is characterized in that a compound of the general formula II

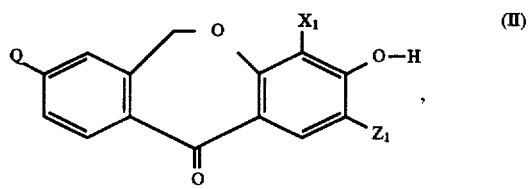

in which Q has the above-mentioned meaning and one of the two residues $X_1$ and $Z_1$ denotes acetyl whereas the other represents hydrogen, $C_1$ to $C_6$ alkyl or $C_2$ to $C_6$ alkenyl, is reacted in a known manner with an oxalic acid derivative such as for example diethyl oxalate under the influence of a base such as for example an alkali alcoholate and cyclized or a compound of the general formula III

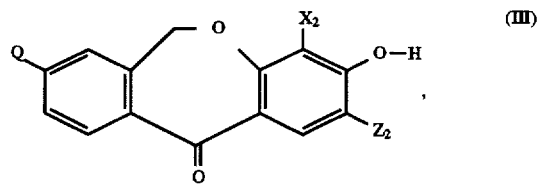

in which Q has the above-mentioned meaning and one of the two residues $X_2$ and $Z_2$ denotes hydrogen whereas the other represents hydrogen, $C_1$ to $C_6$ alkyl or $C_2$ to $C_6$ alkenyl, is reacted in a known manner with a halogenfumaric acid derivative such as for example bromofumaric acid dimethyl ester under the influence of a base such as for example an alkali alcoholate and cyclized, and subsequently, if desired, one or several of the residues Q, R, X and Z are converted into another residue given by the definition and/or converted into a physiologically tolerated salt.

It is expedient to react compounds of formulae II and III in a basic medium such as a lower alcohol like methanol, ethanol or isopropanol in the presence of an alkali alcoholate. The subsequent cyclization is carried out for example in the presence of an acid such as sulphuric acid, polyphosphoric acid, polyphosphoric acid ester or alcoholic hydrochloric acid. In the case that Y and X together form an alkylene residue, the suitable compounds of formula II can be converted directly by acid catalysis into the corresponding compounds of formula I without the action of an oxalic acid derivative.

A conversion of a residue Q into another residue Q defined by the claim is carried out for example by reacting a compound of formula I in which Q represents hydroxyl with an alkylation agent such as for example an alkyl halogenide which is substituted if desired.

An alkoxy group representing Q can, if desired, be converted into a hydroxy group for example by cleaving a methoxy group with boron tribromide.

A carboxyl group can be produced by saponifying an alkoxycarbonyl group contained in Q or Y and Z or Y and X, and an alkoxycarbonyl group can be produced by esterifying a carboxyl group.

If X represents an alkenyl residue then this can be converted, if desired, into an alkyl residue by hydrogenation.

The starting compounds II and III are substances known in the literature or can be produced in analogy to processes known in the literature.

Pharmacologically tolerated salts which come into consideration are in particular alkali, alkaline earth and ammonium salts and, if desired, salts with non-toxic inorganic or organic acids such as e.g. hydrochloric acid, sulphuric acid, phosphoric acid, hydrobromic acid, acetic acid, lactic acid, citric acid, malic acid, benzoic acid, salicylic acid, malonic acid, maleic acid, succinic acid or diaminocaproic acid.

The salts are obtained in the usual manner for example by neutralizing the compounds of formula I with appropriate lyes or acids.

In order to produce pharmaceutical agents, the compounds of the general formula I are mixed in a known manner with suitable pharmaceutical carrier substances, aroma substances, flavourings and dyes and are formed for example into tablets or coated tablets or are suspended or dissolved with the addition of appropriate auxiliary substances in water or oil such as e.g. olive oil.

The substances of the general formula I can be administered orally and parenterally in a liquid or solid form. Water is preferably used as the injection medium which contains the usual stabilizing agents, solubilizers and/or buffers for injection solutions. Such additives are for example tartrate or borate buffer, ethanol, dimethyl-sulfoxide, complexing agents (such as ethylene-diaminetetraacetic acid), high molecular polymers (such as liquid polyethylene oxide) to regulate the viscosity or polyethylene derivatives of sorbitan hydrides.

Solid carrier substances are e.g. starch, lactose, mannitol, methylcellulose, talcum, highly dispersed silicic acid, higher molecular polymers (such as polyethylene glycols).

Suitable preparations for oral administration can if desired contain flavourings and sweeteners. For external application, the substances I according to the invention can also be used in the form of powders and ointments. For this they are for example mixed with powdery, physiologically tolerated diluents or conventional ointment bases. The administered dose depends on the age, health and weight of the recipient, the extent of the disease, the type of other treatments which may be carried out at the same time, the frequency of the treatments and the type of desired effect. The daily dose of the active compound is usually 0.1 to 50 mg/kg body weight. Normally 0.5 to 40 and preferably 1.0 to 20 mg/kg/day in one or several applications per day are effective in order to achieve the desired results.

Apart from the substances mentioned in the examples, the following compounds are preferred within the scope of the invention:

1. 2-Carboxymethoxy-7,13-dihydro-5H-10,12-dioxabenzo [4,5]cyclohepta[1,2-b]naphthalen-5,7-dione-9-carboxylic acid-disodium
2. 7,12-Dihydro-5-propyl-1H-4,13-dioxabenzo[4,5] cyclohepta[1,2-a]naphthalen-1,7-dione-3-carboxylic acid ethyl ester
3. 11-Allyl-7,13-dihydro-2-hydroxy-5H-10,12-dioxabenzo [4,5]cyclohepta-[1,2-b]naphthalen-5,7-dione-9-carboxylic acid ethyl ester
4. 11-Allyl-7,13-dihydro-2-ethoxycarbonylmethoxy-5H-10, 12-dioxabenzo[4,5]cyclohepta[1,2-b]naphthalen-5,7-dione-9-carboxylic acid ethyl ester
5. 11-Allyl-7,13-dihydro-2-octyloxy-5H-10,12-dioxabenzo [4,5]cyclohepta[1,2-b]naphthalen-5,7-dione-carboxylic acid ethyl ester

EXAMPLE 1

7,12-Dihydro-1H-4,13-dioxabenzo [4,5]cyclohepta [1,2-a] naphthalen-1,7-dione-3-carboxylic acid ethyl ester 8.04 g (30 mmol) 4-acetyl-6,11-dihydro-3-hydroxydibenz [b,e]oxepin-11-one is added to a solution of 4.14 g (180 mmol) sodium in 250 ml ethanol, it is heated for 10 minutes to reflux, cooled to room temperature, admixed with 14.6 g (100 mmol) diethyl oxalate, heated for 90 minutes to reflux, allowed to cool and filtered. The precipitate is taken up in 100 ml ethanol, the suspension is saturated with hydrogen chloride and subsequently heated for 1 hour to 50° C. After cooling it is poured onto ice and filtered. 7.8 g of the title compound (74% of theory) of melting point 178°–180° C. (from ethanol) remain.

EXAMPLE 2

The following are obtained in an analogous manner to that described in example 1:

| Name | Yield % | Melting point (solvent) |
|---|---|---|
| a) 7,12-dihydro-10-hydroxy-1H-4,13-dioxabenzo[4,5]cyclohepta[1,2-a]-naphthalene-1,7-dione-3-carboxylic acid-ethyl ester from 4-acetyl-6,11-dihydro-3,8-dihydroxy-dibenz[b,e]oxepin-11-one and diethyl oxalate | 35 | 251–253 (diethyl ether) |
| b) 7,13-dihydro-5H-10,12-dioxabenzo-[4,5]cyclohepta[1,2-b]-naphthalen-5,7-dione-9-carboxylic acid ethyl ester from 2-acetyl-6,11-dihydro-3-hydroxy-dibenz[b,e]oxepin-11-one and diethyl oxalate | 79 | 174–175 (ethanol) |
| c) 7,13-dihydro-2-hydroxy-5H-10,12-dioxabenzo[4,5]cyclohepta[1,2-b]-naphthalen-5,7-dione-9-carboxylic acid ethyl ester from 2-acetyl-6,11-dihydro-3,8-dihydroxy-dibenz[b,e] oxepin-11-one and diethyl oxalate | 77 | 210–212 (ethanol) |
| d) 7,13-dihydro-11-propyl-5H-10,12-dioxabenzo[4,5]cyclohepta[1,2-b]-naphthalen-5,7-dione-9-carboxylic acid ethyl ester from 2-acetyl-6,11-dihydro-3-hydroxy-4-propyl-dibenz[b,e]oxepin-11-one and diethyl oxalate | 84 | 194–196 (ethanol) |
| e) 11-allyl-7,13-dihydro-5H-10,12-dioxabenzo[4,5]cyclohepta[1,2-b]-naphthalen-5,7-dione-9-carboxylic acid ethyl ester from 2-acetyl-4-allyl-6,11-dihydro-3-hydroxy-dibenz[b,e]oxepin-11-one and diethyl oxalate | 79 | 179–181 (ethanol) |
| f) 7,13-dihydro-2-hydroxy-11-propyl-5H-10,12-dioxabenzo-[4,5]cyclohepta-[1,2-b]naphthalen-5,7-dione-9-carboxylic acid ethyl ester from 2-acetyl-6,11-dihydro-3,8-dihydroxy-4-propyl-dibenz[b,e]-oxepin-11-one and diethyl oxalate | 91 | 265–268 (ethanol) |
| g) 7,13-dihydro-2-methoxy-11-propyl-5H-10,12-dioxabenzo[4,5]cyclo-hepta[1,2-b]naphthalen-5,7-dione-9-carboxylic acid ethyl ester from 2-acetyl-6,11-dihydro-3-hydroxy-8-methoxy-4-propyl-dibenz[b,e]oxepin-11-one and diethyl oxalate | 87 | 182–183 (ethanol) |
| h) 11-allyl-7,13 dihydro-2-methoxy-5H-10,12-dioxabenzo[4,5]cyclo-hepta[1,2-b]naphthalen-5,7-dione-9-carboxylic acid ethyl ester from 2-acetyl-4-allyl-6,11-dihydro-3-hydroxy-8-methoxy-dibenz[b,e]-oxepin-11-one and diethyl oxalate | 84 | 156–158 (ethanol) |
| i) 7,13-dihydro-2-methoxy-5H-10,12-dioxabenzo[4,5]cyclohepta[1,2]-naphthalen-5,7-dione-9-carboxylic acid ethyl ester from 2-acetyl-6,11-dihydro-3-hydroxy-8-methoxy-dibenz[b,e]oxepin-11-one and diethyl oxalate | 78 | 223–225 (ethanol) |
| j) 7,12-dihydro-10-methoxy-1H-4,13-dioxabenzo[4,5]cyclohepta[1,2-a]-naphthalen-1,7-dione-3-carboxylic acid ethyl ester from | 76 | 183–185 (ethanol) |

| Name | Yield % | Melting point (solvent) |
|---|---|---|
| 4-acetyl-6,11-dihydro-3-hydroxy-4-methoxy-dibenz[b,e]oxepin-11-one and diethyl oxalate | | |

EXAMPLE 3

7,13-Dihydro-2-octyloxy-5H-10,12-dioxabenzo[4,5]-cyclohepta[1,2-b]naphthalen-5,7-dione-9-carboxylic acid ethyl ester A mixture of 3.7 g (10 mmol) of the compound of example 2 c, 50 ml dimethylformamide, 1.4 g potassium carbonate and 1.75 ml 1-bromooctane is heated for 6 hours to 80° C., subsequently filtered and the filtrate is concentrated by evaporation. It is taken up in ethyl acetate and chromatographed on silica gel (eluting agent:ethyl acetate:isohexane 1:1). After trituration with ether, 2.4 g of the title compound (50% of theory) remains of melting point 103°–105° C.

EXAMPLE 4

The following are obtained in an analogous manner to that described in example 3:

| Name | | Melting point (solvent) |
|---|---|---|
| a) 7,13-dihydro-2-octyloxy-11-propyl-5H-10,12-dioxabenzo-[4,5]cyclohepta[1,2-b]naphthalen-5,7-dione-9-carboxylic acid ethyl ester from the compound of example 2f and octylbromide | 63 | 90–91 (ether) |
| b) 7,13-dihydro-2-ethoxycarbonyl-methoxy-5H-10,12-dioxabenzo-[4,5]cyclohepta[1,2-b]naphthalen-5,7-dione-9-carboxylic acid ethyl ester from the compound of example 2c and bromoacetic acid ethyl ester | 86 | 190–192 (ether) |
| c) 7,13-dihydro-2-ethoxycarbonyl-methoxy-11-propyl-5H-10,12-dioxa-benzo[4,5]cyclohepta[1,2-b]-naphthalen-5,7-dione-9-carboxylic acid ethyl ester from the compound of example 2f and bromoacetic acid ethyl ester | 66 | 151–152 (ethanol) |

EXAMPLE 5

7,13-Dihydro-5H-10,12-dioxabenzo[4,5]cyclohepta[1,2-b] naphthalen-5,7-dione-9-carboxylic acid-sodium 19 ml N sodium hydroxide solution and 30 ml water are added to a solution of 6.65 g (19 mmol) of the compound of example 2b in 150 ml ethanol, it is heated for 30 minutes to 70° C., allowed to cool and the precipitate is filtered. 5.2 g of the title compound (80% of theory) is obtained with a decomposition point above 290° C.

EXAMPLE 6

The following are obtained in an analogous manner to that described in example 5:

| Name | Yield % | Melting point (solvent) |
|---|---|---|
| a) 7,13-dihydro-2-hydroxy-5H-10,12-dioxabenzo-[4,5]cyclohepta[1,2-b]-naphthalen-5,7-dione-9-carboxylic acid sodium from the compound of example 2c | 67 | above 280 (water) |
| b) 7,13-dihydro-2-octyloxy-5H-10,12-dioxabenzo[4,5]cyclohepta[1,2-b]-naphthalen-5,7-dione-9-carboxylic acid sodium from the compound of example 3 | 88 | above 280 (water) |
| c) 7,13-dihydro-2-ethoxycarbonyl-methoxy-5H-10,12-dioxabenzo[4,5]-cyclohepta[1,2-b]-naphthalen-5,7-dione-9-carboxylic acid sodium from the compound of example 4b | 56 | above 280 (water) |
| d) 7,13-dihydro-2-methoxy-5H-10,12-dioxabenzo[4,5]cyclohepta[1,2-b]-naphthalen-5,7-dione-9-carboxylic acid sodium from the compound of example 2i | 47 | above 280 (water) |
| e) 7,12-dihydro-1H-4,13-dioxabenzo-[4,5]cyclohepta[1,2-a]-naphthalen-1,7-dione-3-carboxylic acid sodium from the compound of example 1 | 75 | above 280 (water) |
| f) 7,12-dihydro-10-methoxy-1H-4,13-dioxabenzo[4,5]cyclohepta[1,2-a]-naphthalen-1,7-dione-3-carboxylic acid sodium from the compound of example 2j | 52 | above 280 (water) |

EXAMPLE 7

4-Acetyl-9-methoxy-2-methyl-1,2,6,11-tetrahydro-3,12-dioxabenzo[4,5]cyclohepta[1,2-e]inden-6-one 3.9 g (11 mmol) 2-acetyl-4-allyl-6,11-dihydro-3-hydroxy-8-methoxy-dibenz[b,e]oxepin-11-one is added at 100° C. to a mixture of 9.2 g phosphorus pentoxide and 6 ml ethanol, heated for 30 minutes to 140° C., poured onto ice and filtered. After chromatography on silica gel (eluting agent-:ethyl acetate:isohexane 1:1) 0.9 g of the title compound (23% of theory) of melting point 159°–160° C. (from ether) is isolated.

5-Acetyl-7,12-dihydro-10-methoxy-1H-4,13-dioxabenzo [4,5]cyclohepta[1,2-a]naphthalen-7-one can be detected as a by-product.

EXAMPLE 8

Inhibition of $PLA_2$ activity

The human recombinant type II $PLA_2$ (=synovial $PLA_2$) as a typical representative of a $PLA_2$ was used for the test.

The table shows the percentage in-vitro inhibition of this enzyme by the model compounds of examples 2a), 2c) and 4a). The enzyme was inhibited dose-dependently and 78.61 and 49% inhibition was already achieved with 10 µg/ml.

In contrast the table shows that although indomethacin also inhibited the enzyme, the maximum inhibition was only 52% at the highest concentration of 100 µg/ml. This documents the superiority of the new $sPLA_2$ inhibitors compared to a cyclooxygenase inhibitor.

TABLE

Inhibition of the sPLA₂ enzyme activity by tetracyclic dibenzoxepin derivatives and indomethacin

| Concentrations | Substances | | | |
|---|---|---|---|---|
| | Ex.2c) | Ex.2a) | Ex.4a) | Indomethacin |
| 100 μg/ml | n.d. | n.d. | n.d. | 52 |
| 10 μg/ml | 78 | 61 | 49 | 10 |
| 1 μg/ml | 73 | 52 | 17 | 0 |
| 0.1 μg/ml | 12 | 28 | 16 | n.d |

Means of 3 experiments (duplicate determinations), n.d. = not determined

We claim:

1. Compound of the formula

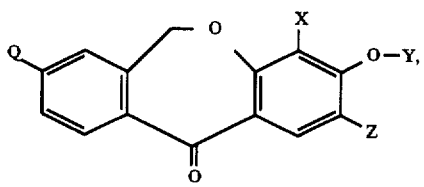

wherein

Q is hydrogen, hydroxy, or a $C_1$–$C_8$ alkoxy group which is unsubstituted or substituted by carboxyl or $C_1$–$C_6$ alkoxycarbonyl; and either Y and Z together from a group

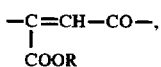

and

X is hydrogen, $C_1$–$C_6$ alkyl or $C_2$–$C_6$ alkenyl, or

Y and X together form a group

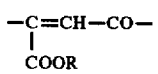

or an alkylene residue of 2–4 carbon atoms, and

Z is hydrogen, $C_1$–$C_6$ alkyl or $C_1$–$C_6$ alkanoyl, where R is hydrogen or an $C_1$–$C_6$ alkyl residue, or a physiologically tolerated salt thereof.

2. Compound of claim 1, wherein the compound is

2-Carboxymethoxy-7,13-dihydro-5H-10,12-dioxabenzo[4,5]cyclohepta[1,2-b]naphthalen-5,7-dione-9-carboxylic acid-disodium 7,12 -Dihydro-5-propyl-1H-4,13-dioxabenzo[4,5]cyclohepta[1,2-a]naphthalen-1,7-dione-3-carboxylic acid ethyl ester 11-Allyl-7,13-dihydro-2-hydroxy-5H-10,12-dioxabenzo[4,5]cyclohepta-[1,2-b]naphthalen-5,7-dione-9-carboxylic acid ethyl ester 11-Allyl-7,13-dihydro-2-ethoxycarbonylmethoxy-5H-10,12-dioxabenzo[4,5]cyclohepta[1,2-b]naphthalen-5,7-dione-9-carboxylic acid ethyl ester or 11-Allyl-7,13-dihydro-2-octyloxy-5H-10,12-dioxabenzo[4,5]cyclohepta[1,2-b]naphthalen-5,7-dione carboxylic acid ethyl ester or a salt or ester thereof.

3. Compound of claim 1, wherein the compound is 7,12-Dihydro-1H-4,13-dioxabenzo[4,5]cyclohepta[1,2-a]naphthalen-1,7-dione-3-carboxylic acid ethyl ester 7,12-dihydro-10-hydroxy-1H-4,13-dioxabenzo[4,5]cyclohepta[1,2-a]naphthalen-1,7-dione-3-carboxylic acid-ethyl ester 7,13-dihydro-5H-10,12-dioxabenzo[4,5]cyclohepta[1,2-b]-naphthalen-5,7-dione-9-carboxylic acid ethyl ester 7,13-dihydro-2-hydroxy-5H-10,12-dioxabenzo[4,5]cyclohepta[1,2-b]-naphthalen-5,7-dione-9-carboxylic acid ethyl ester 7,13-dihydro-11-propyl-5H-10,12-dioxabenzo[4,5]cyclohepta[1,2-b]-naphthalen-5,7-dione-9-carboxylic acid ethyl ester 11-allyl-7,13-dihydro-5H-10,12-dioxabenzo[4,5]cyclohepta[1,2-b]-naphthalen-5,7-dione-9-carboxylic acid ethyl ester 7,13-dihydro-2-hydroxy-11-propyl-5H-10,12-dioxabenzo-[4,5]cyclohepta[1,2-b]naphthalen-5,7-dione-9-carboxylic acid ethyl ester 7,13-dihydro-2-methoxy-11-propyl-5H-10,12-dioxabenzo[4,5]cyclo-hepta [1,2-b]naphthalen-5,7-dione-9-carboxylic acid ethyl ester 11-allyl-7,13-dihydro-2-methoxy-5H-10,12-dioxabenzo[4,5]cyclo-hepta [1,2-b]naphthalen-5,7-dione-9-carboxylic acid ethyl ester 7,13-dihydro-2-methoxy-5H-10,12-dioxabenzo[4,5]cyclohepta[1,2-b]naphthalen-5,7-dione-9-carboxylic acid ethyl ester or 7,12-dihydro-10-methoxy-1H-4,13-dioxabenzo[4,5]cyclohepta[1,2-a]naphthalen-1,7-dione-3-carboxylic acid ethyl ester or a salt or ester thereof.

4. Compound of claim 1, wherein the compound is 7,13-Dihydro-2-octyloxy-5H-10,12-dioxabenzo[4,5]cyclohepta[1,2-b]naphthalen-5,7-dione-9-carboxylic acid ethyl ester 7,13-dihydro-2-octyloxy-11-propyl-5H-10,12-dioxabenzo-[4,5]cyclohepta[1,2-b]naphthalen-7-one-9-carboxylic acid ethyl ester 7,13-dihydro-2-ethoxycarbonylmethoxy-5H-10,12-dioxabenzo-[4,5]cyclohepta[1,2-b]naphthalen-5,7-dione-9-carboxylic acid ethyl ester 7,13-dihydro-2-ethoxycarbonylmethoxy-11-propyl-5H-10,12-dioxabenzo[4,5]cyclohepta[1,2-b]-naphthalen-5,7-dione-9-carboxylic acid ethyl ester 7,13-Dihydro-5H-10,12-dioxabenzo[4,5]cyclohepta[1,2-b]naphthalene-5,7-dione-9-carboxylic acid-sodium 7,13-dihydro-2-hydroxy-5H-10,12-dioxabenzo-[4,5]cyclohepta[1,2-b]-naphthalen-5,7-dione-9-carboxylic acid sodium 7,13-dihydro-2-octyloxy-5H-10,12-dioxabenzo[4,5]cyclohepta[1,2-b]-naphthalen-5,7-dione-9-carboxylic acid sodium 7,13-dihydro-2-ethoxycarbonylmethoxy-5H-10,12-dioxabenzo[4,5]-cyclohepta[1,2-b]-naphthalen-5,7-dione-9-carboxylic acid sodium 7,13-dihydro-2-methoxy-5H-10,12-dioxabenzo[4,5]cyclohepta[1,2-b]naphthalen-5,7-dione-9-carboxylic acid sodium 7,12-dihydro-1H-4,13-dioxabenzo-[4,5]cyclohepta[1,2-a]-naphthalen-1,7-dione-3-carboxylic acid sodium 7,12-dihydro-10-methoxy-1H-4,13-dioxabenzo[4,5]cyclohepta[1,2-a]-naphthalen-1,7-dione-3-carboxylic acid sodium or 4-Acetyl-9-methoxy-2-methyl-1,2,6,11-tetrahydro-3,12-dioxabenzo[4,5]cyclohepta[1,2-e]inden-6-one
or a salt or ester thereof.

5. A method of inhibiting phospholipase in a patient in need of such inhibition, said method comprising administering to said patient a phospholipase-inhibiting amount of a compound of claim 1.

6. Method of claim 5, wherein the compound is 7,13-dihydro-2-hydroxy-5H-10,12-dioxabenzo[4,5]cyclohepta[1,2-b]-naphthalen-5,7-dione-9-carboxylic acid ethyl ester 7,12-dihydro-10-hydroxy-1H-4,13-dioxabenzo[4,5]cyclohepta[1,2-a]-naphthalen-1,7-dione-3-carboxylic acid-ethyl ester or 7,13-dihydro-2-octyloxy-11-propyl-5H-10,12-dioxabenzo-[4,5]cyclohepta[1,2-b]naphthalen-5,7-dione-9-carboxylic acid ethyl ester or a salt or ester thereof.

7. A pharmaceutical composition suitable for the inhibition of phospholipase comprising a compound of claim 1 and a pharmaceutically acceptable carrier therefor.

* * * * *